United States Patent [19]

Johnsen et al.

[11] Patent Number: 5,605,841
[45] Date of Patent: Feb. 25, 1997

[54] SYSTEM FOR AUTOMATIC SAMPLE ANALYSIS AND A METHOD FOR PRODUCING THE SYSTEM INCLUDING A CLEANING UNIT FOR A MOVABLE OPTICAL HEAD

[75] Inventors: Erik Johnsen, Vejle; Jens Heinrichson, Give; Michael Bjerre, Vejle, all of Denmark

[73] Assignee: Jesma-Matador A/S, Vejle, Denmark

[21] Appl. No.: 335,762

[22] PCT Filed: May 14, 1993

[86] PCT No.: PCT/DK93/00165

§ 371 Date: Nov. 14, 1993

§ 102(e) Date: Nov. 14, 1993

[87] PCT Pub. No.: WO93/23731

PCT Pub. Date: Nov. 25, 1993

[30] Foreign Application Priority Data

May 14, 1992 [DK] Denmark .................. 0644/92

[51] Int. Cl.$^6$ .................. G01N 1/20; G01N 21/01; G01N 21/15
[52] U.S. Cl. .................. 436/164; 436/43; 422/62; 422/63; 422/82.05; 250/341.8; 250/339.11; 250/910; 359/507
[58] Field of Search .................. 422/62, 63, 68.1, 422/74, 82.05; 436/20, 22, 43, 49, 164, 175; 359/507, 508; 356/436, 439, 442; 250/343, 241.8, 341.8, 339.11, 341.1, 910

[56] References Cited

U.S. PATENT DOCUMENTS

| | | | |
|---|---|---|---|
| 3,677,652 | 7/1972 | Little | 356/183 |
| 3,869,213 | 3/1975 | Greene | 356/244 |
| 4,575,240 | 3/1986 | Hess et al. | 356/246 |
| 4,742,228 | 5/1988 | Bischoff | 250/341 |
| 5,324,949 | 6/1994 | Johnsen | 250/341 |
| 5,406,084 | 4/1995 | Tobler et al. | 250/339.01 |

FOREIGN PATENT DOCUMENTS 8911090  11/1989  WIPO.

*Primary Examiner*—Long V. Le
*Attorney, Agent, or Firm*—Antonelli, Terry, Stout & Kraus, LLP

[57] ABSTRACT

A system for on line analysis of material samples in accordance with the invention includes a grinding mill for comminuting sample material to output comminuted sample material; an analyzer unit for performing the on line analysis of the outputted comminuted sample material and having a housing holding an optical system having a front glass with the optical system performing the on line analysis of the outputted comminuted sample material, and a receiving chamber for receiving the outputted comminuted sample material from the grinding mill; and a mechanism for moving the housing relative to the receiving chamber between a first position at which the front glass closes a wall opening into the receiving chamber and a second position at which the front glass is cleaned by a cleaning mechanism.

16 Claims, 2 Drawing Sheets

SYSTEM FOR AUTOMATIC SAMPLE ANALYSIS AND A METHOD FOR PRODUCING THE SYSTEM INCLUDING A CLEANING UNIT FOR A MOVABLE OPTICAL HEAD

BACKGROUND OF THE INVENTION

1. Field of the Invention

The present invention relates to a sampling and analysing equipment for use in systems for receiving raw materials, in particular biological materials for delivery in a mixed or a processed condition in smaller portions or delivering materials in mixed or processing condition.

2. Description of the Prior Art

In WO/89/11090 is already described the advantages of using an automatic sampling equipment already described, from which samples of newly received materials can be rapidly transferred to a central analysing station, wherein the single samples are quickly analysed, thus enabling a quality determination of the new materials as a basis for a correct accounting in view of the qualities as well as for a rapid adjustment of processing or mixing conditions, should the new materials exhibit changed properties, regarding their content of fat, water or protein. A typical relevant application in preparation of fodder mixtures for livestock.

The equipment disclosed in the aforementioned WO publication is relatively expensive, and it is well applicable in large applications. In practice it is not suited for use in smaller applications, where it is an economical burden to arrange for automatic samplers and a pneumatic conveyor system between the sampling system and the analysing equipment. At least to a certain extent it is fully acceptable to manually carry the samples to the analysing equipment with the latter being simplified.

SUMMARY OF THE INVENTION

In connection with the invention it has been recognized that in fact it is possible to modify existing laboratory equipment to make it usable for automatic, successive samples handling and analysing, such that with a relatively modest investment it is still possible to achieve a noticeable increase of the analysing capacity with a minimum of labouring.

Two laboratory units are usable for this purpose, vis. an analyzer based on the so-called NIR principle and a grinding mill for comminuting the material to be analysed. In their known standard designs both of these units require a careful manual cleaning prior to each new operation. With the invention it is important that the required cleaning can take place automatically immediately after each operation such that the equipment will rapidly be ready for handling a new material sample without the new material sample being unduly contaminated by remnants of the previously handled sample material.

The commonly used grinding mills are unfit for cleaning in a sample and automatic manner. These mills have a knife rotor rotating inside a surrounding screen, outside of which there is an annular bowl for receiving the comminuted material. This bowl unit is made with rather sharp inner corners. Even if it is reasonably easy to clean manually, it will be difficult to clean in any simple, automatic way. According to the invention such a mill may be modified to form an automatically easily sealable unit, viz. by replacing the bowl unit with rigid insert parts, which, together define a receiver chamber having an evenly curved outer wall which is much easier to clean than the conventional bowls with sharp edges with the use of air nozzles. The insert parts may form a tangential outlet, thus enabling the mill to work on-line.

The laboratory units for NIR analysing comprise a cabinet having an optical head against which can be placed a cuvette holding a few grams of the material that is to be analysed upon being comminuted. After each operation the cuvette should be cleaned with spirits with all handling being performed manually. According to the invention it is possible to modify these units to an automatic on-line operation. It is an important aspect of the invention that the units are modified standard units owned by users desiring to change into automatic sample handling and analyzing. The reason for this is that such a user will already have spent a considerable amount of capital for achieving a good calibration of the measuring apparatus which requires a high number of expensive chemical analyzes. The detailed calibration base will be inseparably associated with the individual apparatus. For this reason it is highly advantageous that it is the already existing apparatus which is being modified. It has been found to be permissible to move the associated optical head to a different apparatus unit in order to make possible an automatic sample handler.

Similar but less stringent circumstances apply to the grinding mill. If strictly required a mill may be replaced by another mill, but preferable only of the same brand and type, because the accuracy of the resulting analysis is closely dependent upon the samples being prepared in the same manner as when the calibrations were made.

With the use of the relatively inexpensive laboratory mills it is possible to handle materials with a coarseness up to about pea size. With the invention it has been found possible to work with sample portions considerably smaller than the approximately four liters as specified in the WO/89/11090, viz. 200–300 ml. The samples may be supplied from external samplers or sample terminals via pneumatic conveying. Owing to their small volume and the limited capacity of the system it will normally be acceptable to just scrap the samples without returning them.

If with a given user still coarser materials are to be handled, it will be required to pre-prepare these materials by comminution to the fineness required for an effective milling in the aforementioned grinding mill. This can be arranged in the conventional manual manner with the use of a suitable chopping machine. However, according to the invention, it will also be possible to arrange this chapping unit as an on-line module in operative connection with the basic system of the mill and the analyzer. As in WO/89/11090, this module may be connected with various automatic samplers and sample terminals. It is preferred to work with sample portions of the magnitude of four liters. The module may comprise a divider that sends a smaller sample, e.g. 250 ml, to the mill and analyzer, while the major part of the sample, 3.75 l, may be returned or scrapped.

The basic system may be supplemented by a receiver unit for the analysed samples. The receiver unit may easily be adapted so as to distinguish between sample refuse to be scrapped and sample portions which, from an analyzing standpoint, are more interesting, such that they should be collected for further reference analysis.

BRIEF DESCRIPTION OF THE DRAWINGS

The invention, which is defined in more detail in the claims, will now be further explained with reference to the drawing, in which:

Description of the Preferred Embodiments

Figure 1:
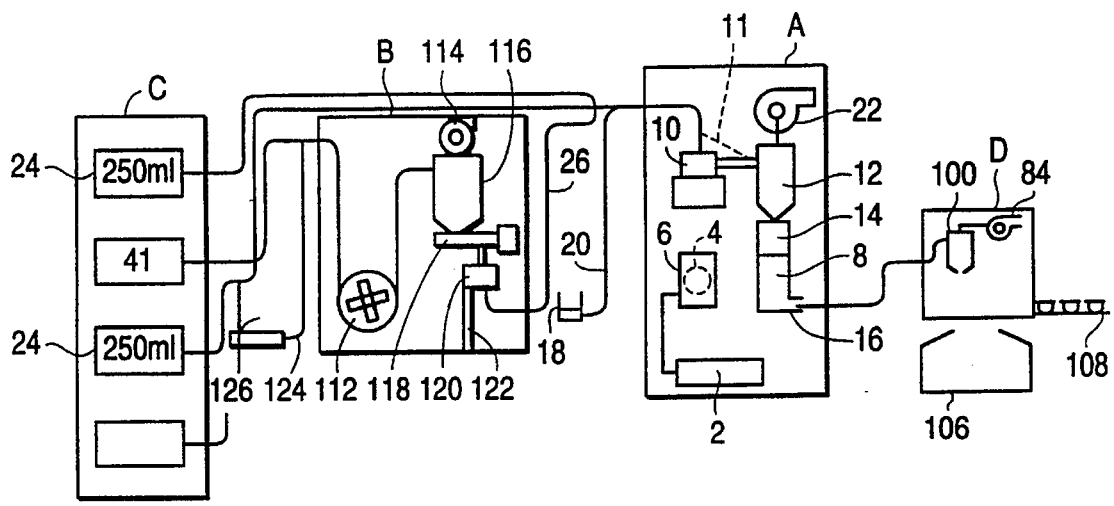
FIG. 1 is a schematic diagram of a system according to the invention.

The system shown in FIG. 1 is basically divided in A, B, C, and D. Section A is the basic module in the system is which the user switches from a manual laboratory handling of arriving samples to a fully automatic handling thereof with a maintained calibration of a previously used analysing unit based on the NIR principle or principles comparable thereto.

An already existing NIR analyzer 2 is located in Section A with its optical head 4 taken out and mounted in a cabinet 6, which is movable relative to a test chamber 8 as described below. This chamber receives comminuted sample material from a mill 10 with the sample material passing through a cyclone 12 and then to a homogenizer 14. After the analysis the samples are conveyed through a bottom outlet 16 of the chamber 8, optionally to the module D, which is described in more detail below.

The mill 10 can be supplied with test material from receiver terminal 18, from which the material is supplied through a conduit 20, driven by the suction of a suction fan 22, which, in Section A, draws conveying air from the mill 10 to the cyclone 12. However, the supply conduit 20 may also be connected to external samplers or terminals 24 in section C as well as to a discharge conduit 26 from section B.

Figure 2:
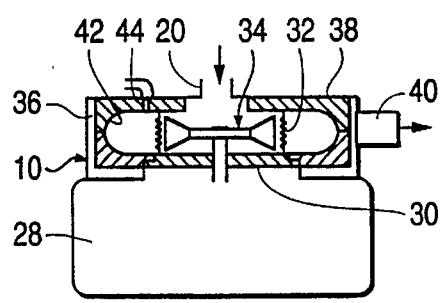
FIG. 2 is a sectional view of a grinding mill therein.

If applicable, the mill 10 may be a previously used laboratory mill, which is then only modified according to the invention as illustrated in FIG. 2. Such a mill will typically have a lower motor housing 28 with a central top mounting 30 having along its periphery an vertical standing annular screen 32 having an inner side of which is swept by a knife rotor 34. A tray member 36 surrounds the screen 32 and is closable, in the original design, by a cover not shown. According to the invention, the tray 36 is replaced or filled out with an annular body 38, shown in hatching, which is made with a tangential outlet 40 and cross sectionally shaped with an evenly curved inner wall 42. This annular body is at plural places provided with compressed air nozzles 44 enabling an effective cleaning of the chamber after each passage of a sample.

A supplied sample after a remainder is blown off is conveyed from the mill 10 suitably comminuted, via the cyclone 12, to the homogenizer 14. The homogenizer 14 serves the same purpose as the unit designated 5 in FIG. 4 of WO89/09388, which homogenizes the received material therein. In the present invention, however, a different unit is used, viz. an apparatus working according to a known principle as a real mixing unit which is used only for self-mixing of the successively supplied samples. It has been found that it is then possible to avoid the use of the special measuring homogenizer which according to the WO publication is provided inside the test chamber as identified by reference numerals 36, 38.

Because the mixing unit is of a known type, it is only briefly described. According to FIG. 4 it comprises a horizontal cylindrical housing 50 accommodating a rotor 52, which for an outer worm winding 54 with a conveying pitch in one direction and an inner worm winding with a pitch in the opposite axial direction. It is known that more materials fed to the top of the rotor housing 50 can be effectively mixed. According to the invention a very effective sample homogenizing of only a single material can be achieved. In connection with the invention, the known mixing principle will provide not only for a good homogenizing of the received single material but also for a relatively small contact area between the material and the respective working units, such that the risk of sample contamination from previous samples can be kept as low as possible.

From the fine homogenizer 14 the discharge material is fed down into the analysing unit 6, 8, which, in principle, may be designed just as disclosed in the WO publication. It should be mentioned, however, that in connection with the invention it has been found possible to simplify also this part of the entire system, so as to obviate the use of a complicated and operatively expensive feeding of a separation film between the sensor head of the analyzer and the sample material. This is achieved by effecting a cleaning of the sensor head by blowing, wiping or ionizing of the head, which in a NIR based system will exhibit a cover disk of quartz glass. It is sufficient to clean the outside of this disk between the analyzing of the successive sample portions. A wiping can be effected with a moving cleaning web attached to a roller which is moved along the outside of the quartz glass, such that the wiping will take place in a progressive and concentrated manner As mentioned, but not shown in more detail, there are mounted, at all qualified places in the system, air nozzles for interior cleaning and flushing of the different units.

The numeral 11 denotes a connection for by-passing the mill for supplying products not requiring to be milled.

Figure 4:
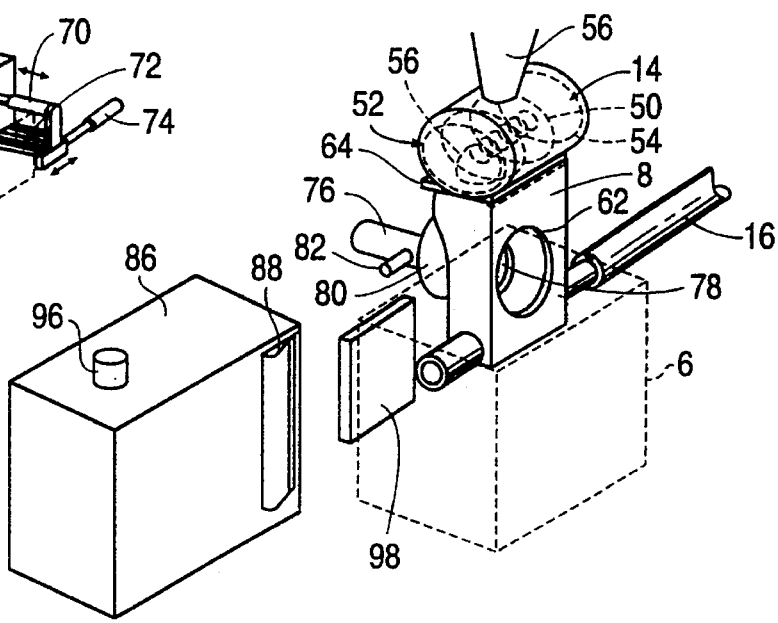
FIGS. 4–6 are other views thereof.
Figure 5:
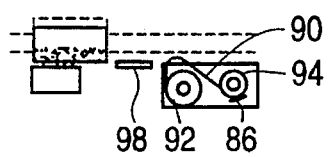
Figure 6:
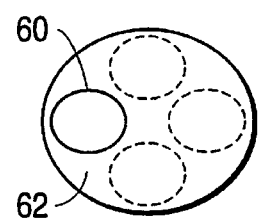

With the invention it is a basic consideration that the use of the mixing unit 14 as shown in FIGS. 1 and 4, downstream of the cyclone 12, provides a high degree of homogenization of the treated samples to be achieved, such that each of the samples, when deposited into the underlying test chamber 8, will remain sufficiently homogenous for the analysing measurements to be correct. For the same reason, however, it is preferred that the measuring window in the test chamber be relatively large, viz. so much larger than the required measuring area that there is area sufficient for making separate tests on two or more different areas of the window, e.g. as illustrated in FIG. 6. It is possible to effect a successive shift of the sensor head, designated 60, relative to the test chamber. If in this way, e.g. four measurements are made at different places of one single sample, a representative average result can be obtained. The associated data processor may trigger an alarm, if the difference between the single measuring results is unacceptably high, indicating that the homogenization is not good enough. If so, it is possible to repeat the test with a new sample of the same material, or to take out the sample for chemical analysis.

Figure 3:
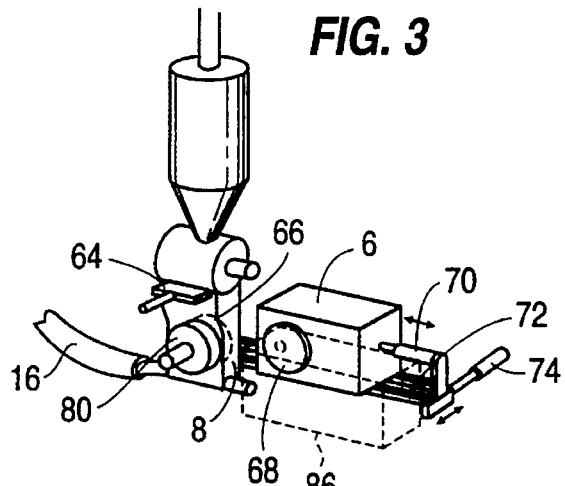
FIG. 3 is a perspective view of an associated NIR analyzer.

When the test window, 62 is thus required to be relatively large, the test chamber will have to be correspondingly high and wide. With sample portions of the magnitude 250 ml, the chamber then has to be so thin, (See FIGS. 3 and 4), that it will be thinner than the outlet opening beneath the homogenizer 14. IN order to counteract a separation in the sample material it is desirable that the entire sample be deposited at one time into the test chamber 8. This may be accomplished by a sudden retraction of a valve plate 64 at the outlet from the homogenizer 14. Due to the reduced thickness of the chamber 8, there has to be a certain narrowing 66 downwardly. It will be noted that this narrowing is located above the chamber side opposite the test window 62. The reason for this positioning is that the depositing of the material next to this window should preferably be as direct and undisturbed as possible.

In the analyzer equipment as shown in FIGS. 3–6, the measuring window 62 is a regular hole in the wall of the test chamber 8, while the associated window glass, designated 68, is mounted on the apparatus cabinet 6 containing the measuring optics 4 for effecting the analyses. Inside this unit the optical head 4 is mounted in such a manner that it can be moved between the four different positions shown in FIG. 6. In addition, the whole cabinet 6 is mounted on a movable support 72 which is displaceable by means of a cylinder 70, while the support 72 is transversely displaceable by means of a cylinder 74. It is possible to move the cabinet 6 in FIG. 3 a distance to the left and thereafter forwardly against the test chamber, until the window 68 seals over the hole in the wall of the test chamber, which can thereafter receive a sample to be analysed.

Upon the depositing of the prepared sample portion from the chamber 14 to the test chamber 8 a projection of a piston plate 78 from the rear side of the chamber 8 is arranged by means of a cylinder 76, where this plate is housed in a housing portion 80, such that the sample material adjacent the window 68 is compacted against this window. During the analysing process the sample material should be kept absolutely undisturbed. It is preferred, therefore, to stop the piston plate 78 firmly in its projecting position which is accomplished by means of a crosswise arranged pressure cylinder 82 on the piston cylinder 76.

When the analysis has been made, i.e. when measurements have been made with the measuring head in the respective four positions according to FIG. 6, the piston plate 78 is retracted into the housing part 80, and the discharge pipe 16 is connected with a suction fan for sucking out the sample with preferably the suction fan 84 being located in the discharge section D. The fan may be an ordinary vacuum cleaner. The test chamber will be emptied from below.

After the emptying of the test chamber an important method step is performed, which is not further illustrated, viz. a blowing in of compressed air through air nozzles in or against strategic places in the entire system 14, 8, so as to achieve an effective cleaning of the surfaces which have been in contact with the test material. It should be stressed that in addition to stationary nozzles one or more nozzles may be mounted in connection with the driving shaft of the rotor in the homogenizer 14. Another measure will be to arrange for an extra powerful blast of air sweeping of the window glass 68, as the material being positively pressed thereagainst. The same applies to the piston plate 78. However, for NIR analyses, this will be less critical, because small remnants on this plate will not effectively contaminate the subsequent sample. However, if the analysis is based on a view of illumination through the test chamber, i.e. where also the said plate is translucent, this plate should of course also be effectively cleaned.

After this cleaning it could be possible to continue with the next sample, given that a relevant accuracy standard for the analysis of the next sample can be observed. However, this will be possible only exceptionally, as it will normally be required to ensure an extra good cleaning of the analyzer window glass 68. It is primarily for this reason that the analyzer 6 is mounted in a movable manner so that it will then be possible to expose the window for an external and more effective cleaning thereof.

For achieving this cleaning there is mounted, next to the test chamber 8, as separate, box-shaped unit 86, (See particularly FIGS. 4 and 5), having at its front side a projecting roller 88 acting as a sprocket roller for a cleaning web 90, which is reeled off from a supply reel 92 and is reeled onto a reel driven by a stepmotor 96 as illustrated in FIG. 4. The cleaning web 90 may be a non-expensive, impregnated paper or textile web, which, for each operation, will only have to be advanced as far or as to expose a clean web portion on the roller 88.

With the said movability of the analyzer 6 it will be possible to move this unit such that its window member 68 is brought to scrape over the roller 88, whereby remaining sample resting thereon will be cleaned of effectively. Normally, it will not be required to advance the cleaning web during this operation, as the web will be smudged very little during this operation. Some trace of impregnation agent may be left on the window. If this affects the result of the next analysis, the window will have to be dried or wiped before it is brought to a renewed operative connection with the window hole 62. This is possible by moving the window past special air nozzles or past a wiping unit corresponding to the unit 86.

In the system is also arranged a special measuring plate 98, (See FIGS. 4 and 5), contacts the window member 68 on the analyzer unit 6 may be brought to contact by a suitable moving of this unit. The plate 98 is a ceramic which, when subjected to an analysing measurement, provides known reference results to permit checking of whether the cleaning and the operation of the measuring equipment is correct.

Figure 7:
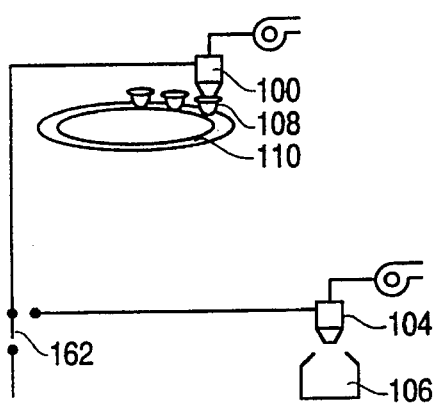
FIG. 7 is a perspective view of a sample discharge station in the system.

IN the discharge section D the sample material is sucked to a cyclone 100, from which it is be delivered to cups 108 on a conveyor 110. See FIG. 7. Alternatively, by means of a switch over valve 102 the material may be fed to a cyclone 104, from which it is discharged to be scrapped. A controller computer may control an emptying into a cup 108 when an analysis result is found so peculiar that a subsequent laboratory analysis of the sample is referred. Suitably, therefore, this part of the system may be mounted directly at or in a laboratory, possibly at a distance from the cyclone 104.

The module B of FIG. 1, is a coarse milling unit containing a knife mill 112 and a suction fan 114 for sucking the sample material to this mill and further sucking the product to a cyclone 116, which, via a discharge unit 118, is delivered to a divider 120. It is preferred to feed the module B with sample portions of approximately 4 1, and the divider 120 should deliver approximately 250 ml to the module A through the conduit 26, i.e. for each sample the divider delivers 3.75 1 through a discharge conduit 112, from which the material may optionally be returned to the relevant source, e.g. a silo.

A suction conduit 124 to the mill 112 in module B may be connected with a local sample receiver 126. It is also a possibility that the conduit can be connected with various automatic samplers or external sample terminals in the system designated C.

In addition to the cleaning by means of compressed air at strategic places in the system, in order to keep the system clean, the various parts thereof, particularly the mill 10 and the cyclone 12, should be kept warm to counteract condensation of sample material on the inner sides.

We claim:

1. A system for on line analysis of material samples comprising:

a grinding mill for comminuting sample material to output comminuted sample material;

an analyzer unit for performing the on line analysis of the outputted comminuted sample material and having a housing holding an optical system having a front glass with the optical system performing the on line analysis of the outputted comminuted sample material and a receiving chamber for receiving the outputted comminuted sample material from the grinding mill; and a mechanism for moving the housing relative to the receiving chamber between a first position at which the front glass closes a wall opening into the receiving chamber and a second position at which the front glass is cleaned by a cleaning mechanism.

2. A system in accordance with claim 1 wherein the cleaning mechanism comprises:

a cleaning housing which is moveable relative to the housing holding the optical system;

an impregnating cleaning web projecting from the cleaning housing for cleaning the front glass of the optical system as the cleaning housing is moved relative to the housing holding the optical system between the first and second positions; and a driving mechanism for advancing the web.

3. A system in accordance with claim 1 wherein:

the optical system is disposed behind the front glass in the housing and has a plurality of operative positions with the optical system being shifted between the operative positions to analyze at least one sample.

4. A system in accordance with claim 1 wherein:

the receiving chamber receiving samples of the outputted comminuted sample material having a volume between 200 to 500 ml.

5. A system in accordance with claim 1 further comprising:

a homogenization mixer disposed above the receiving chamber and coupled to the mill for mixing the outputted comminuted sample material and supplying mixed outputted comminuted sample material to the receiving chamber.

6. A system in accordance with claim 5 wherein the mixer comprises:

a double screw cylindrical mixer.

7. A system in accordance with claim 1 wherein the mill comprises:

a laboratory mill having a screen, an insert portion, disposed adjacent the screen, defining an annular channel between the screen and the insert portion and having an outer rounded wall and a tangential outlet; and inlets within the insert portion for receiving compressed air.

8. A system in accordance with claim 7 further comprising:

a heater within the insert portion.

9. A system in accordance with claim 1 further comprising:

a plurality of modular units, one of the modular units containing the analyzer unit and another modular unit containing another grinding mill for processing larger volume samples than samples processed by the grinding mill for comminuting sample material; and the another modular unit further comprising a divider for separating a portion of the comminuted sample material and discharging the separated portion to the one modular unit containing the analyzer unit.

10. A system in accordance with claim 9 wherein:

the portion ranges from between $1/10$ to $1/25$ of a sample material contained within the another mill.

11. A system in accordance with claim 9 further comprising:

a plurality of samplers coupled to the modular units with the samplers delivering samples to the mills with the samplers delivering samples of a smaller volume to the modular unit containing the grinding mill and of a larger volume to the another grinding mill.

12. A system in accordance with claim 10 further comprising:

a plurality of samplers coupled to the modular units with the samplers delivering samples to the mills with the samplers delivering samples of a smaller volume to the modular unit containing the grinding mill and of a larger volume to the another grinding mill.

13. A system in accordance with claim 1 further comprising:

a discharge unit connected to the analyzing unit to deliver portions of analyzed comminuted sample material selectively to a scrap container or to at least one additional container for collecting the analyzed comminuted sample material for further analysis.

14. A method for on-line analysis of material samples with a system having a grinding mill for comminuting sample material samples to output comminuted material samples, an analyzer unit for performing the on-line analysis of the outputted comminuted material samples and having a housing holding an optical system including an optical head and a front glass with the optical system performing the on-line analysis of the outputted comminuted material samples and a receiving chamber for receiving the outputted comminuted material samples from the grinding mill, and a mechanism for moving the housing relative to the receiving chamber between a first position at which the front glass closes a wall opening into the receiving chamber and a second position at which the front glass is cleaned by a cleaning mechanism comprising:

modifying an existing laboratory equipment by removing the optical head from the existing laboratory equipment and mounting the optical head in the housing in operative connection with the receiving chamber while maintaining an electrical connection between the optical head and the analyzer unit and an original calibration of the analyzer;

using the grinding mill to output a comminuted material sample;

providing the comminuted material sample to the receiving chamber and performing tests on the comminuted material sample with the optical head in the receiving chamber using the original calibration; and moving the housing between the first and the second position after each analysis operation.

15. A method according to claim 14, wherein:

the existing laboratory equipment is modified in that an existing grinding mill therein having a circular screen is used for maintaining the original calibration and is modified to have an insert portion disposed adjacent the screen and an annular channel between the screen and the insert portion and having an outer rounded wall and a tangential outlet as well as inlets for receiving compressed air for cleaning purposes and is used as the grinding mill to output the comminuted material sample.

16. A method for on-line analysis of material samples with a system having a grinding mill for comminuting sample material samples to output comminuted material samples, an analyzer unit for performing the on-line analysis of the outputted comminuted material samples and having a housing holding an optical system including an optical head and a front glass with the optical system performing the on-line analysis of the outputted comminuted material samples and a receiving chamber for receiving the outputted comminuted material samples from the grinding mill, and a mechanism for moving the housing relative to the receiving chamber from and to a first position at which the front glass closes a wall opening into the receiving chamber, comprising:

performing an analysis of a material sample with the housing in the first position;

subsequently moving the housing into a second position of which the front glass is cleaned by a cleaning mechanism; and moving the housing with the cleaned front glass back to the first position preparatory to a subsequent analysis operation of a new material sample.

* * * * *